United States Patent

Kaiser et al.

[11] 3,947,404
[45] Mar. 30, 1976

[54] DIHYDRODIGOXIN COMPOUNDS AND THERAPEUTIC COMPOSITIONS

[75] Inventors: Fritz Kaiser, Lampertheim; Wolfgang Schaumann, Heidelberg; Kurt Stach, Mannheim-Waldhof; Wolfgang Voigtlander, Viernheim, all of Germany

[73] Assignee: Boehringer Mannheim GmbH, Mannheim-Waldhof, Germany

[22] Filed: June 5, 1973

[21] Appl. No.: 367,312

[30] Foreign Application Priority Data
July 6, 1972 Germany............................ 2233147

[52] U.S. Cl.............................. 260/210.5; 424/182
[51] Int. Cl.² ......................................... C07J 19/00
[58] Field of Search ................................ 260/210.5

[56] References Cited
UNITED STATES PATENTS

| | | | |
|---|---|---|---|
| 3,538,078 | 11/1970 | Kaiser et al. | 260/210.5 |
| 3,712,884 | 1/1973 | Voigtlander et al. | 260/210.5 |
| 3,816,403 | 6/1974 | Eberlein et al. | 260/210.5 |

FOREIGN PATENTS OR APPLICATIONS

| | | | |
|---|---|---|---|
| 863,325 | 6/1962 | France | 260/210.5 |

OTHER PUBLICATIONS
Turner, Richard B. "Structure and Syn. of Cardiac Genins," Chemical Reviews, Vol. 43 Aug.–Dec. 1948.

Primary Examiner—Johnnie R. Brown
Assistant Examiner—Cary Owens
Attorney, Agent, or Firm—Burgess, Dinklage & Sprung

[57] ABSTRACT

New dihydrodigoxin derivatives of the formula

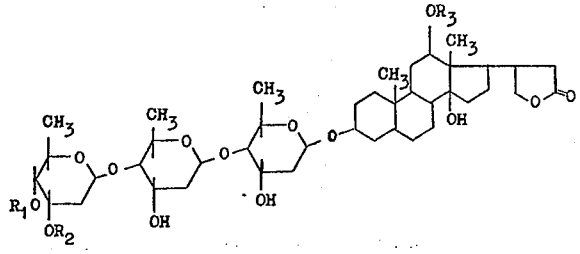

wherein one of $R_1$ and $R_2$ represents a methyl or ethyl radical and the other represents hydrogen, methyl, ethyl or acetyl (i.e. alkanoyl); and $R_3$ is hydrogen or an acetyl group; are outstandingly effective for therapy of cardiac insufficiencies, particularly via peroral administration.

10 Claims, No Drawings

DIHYDRODIGOXIN COMPOUNDS AND THERAPEUTIC COMPOSITIONS

The present invention is concerned with new dihydrodigoxin compounds and with therapeutic compositions containing them.

The new compounds of the invention are derivatives of dihydrodigoxin and have the formula:

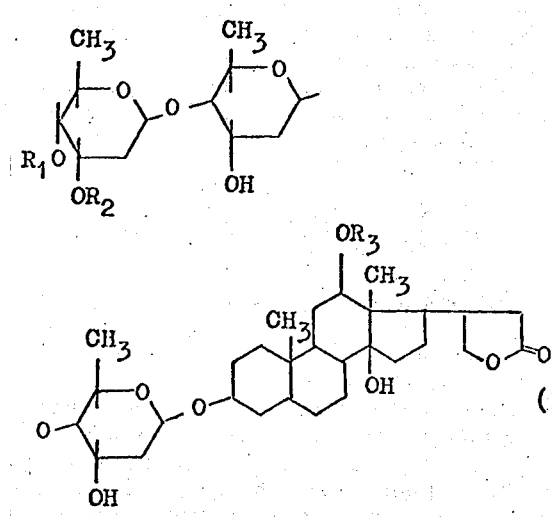

(I), wherein one of $R_1$ and $R_2$ represents a methyl or ethyl radical and the other represents hydrogen, methyl, ethyl or acetyl (i.e. alkanoyl); and $R_3$ is hydrogen or an acetyl group. The acetyl (alkanoyl) radicals are preferably lower, i.e., containing up to 6 carbon atoms.

We have found that these new cardenolide glycoside derivatives are, surprisingly, resorbed more quickly and completely than dihydrodigoxin. They are, therefore, especially suitable for a peroral administration for the therapy of cardiac insufficiencies. Furthermore, the new compounds surprisingly show a central stimulation in doses which do not bring about cardiac effects which are typical for Digitalis glycosides.

The new compounds according to the present invention can be prepared, for example, by one of the following methods:

a. catalytic hydrogenation of compounds of the general formula:

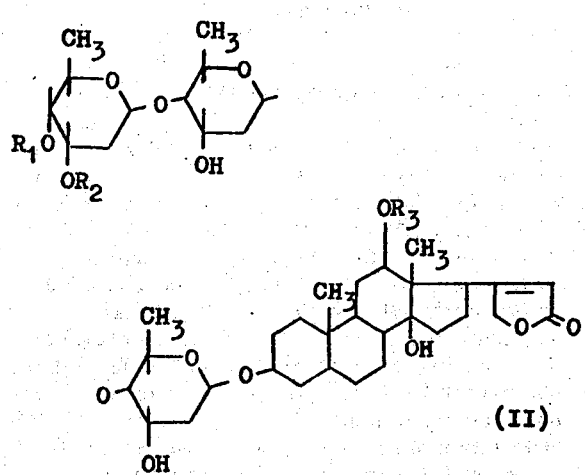

(II)

wherein $R_1$, $R_2$ and $R_3$ have the same meanings as above; or b. methylation or ethylation of compounds of the general formula:

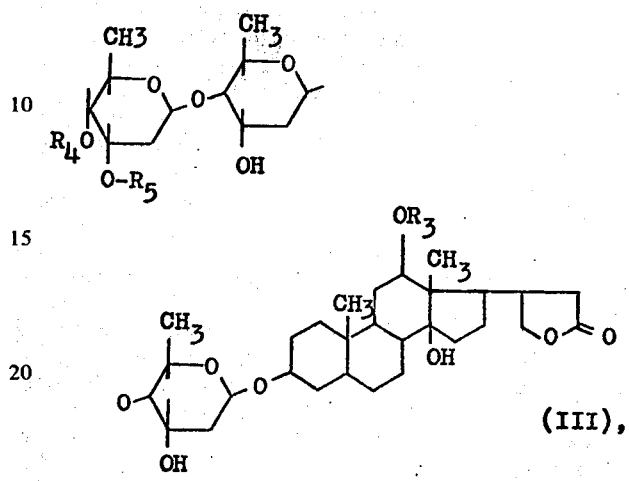

(III), wherein one of the symbols $R_4$ and $R_5$ represents a hydrogen atom and the other one represents a hydrogen atom or a methyl, ethyl or acetyl radical and $R_3$ has the same meaning as above; or c. acetylation of compounds of the general formula:

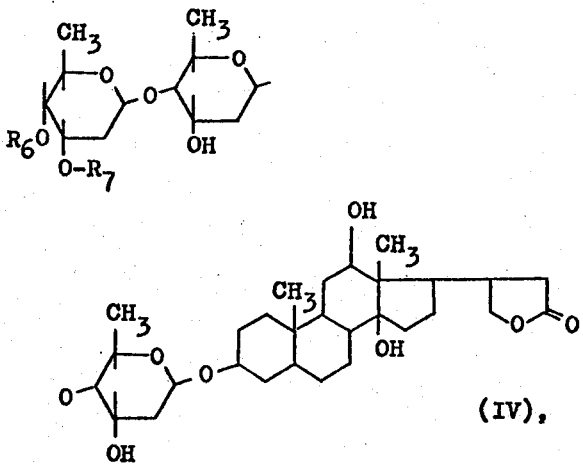

(IV), wherein one of the symbols $R_6$ and $R_7$ represents a methyl or ethyl radical and the other one represents a hydrogen atom.

The catalytic hydrogenation according to method (a) is carried out in known manner, preferably with the use of a noble metal catalyst, for example platinum oxide or colloidal platinum, in a polar solvent, for example, in a lower alcohol or in an ether.

For the methylation or ethylation of compounds of general formula (III), there can be used the appropriate diazoalkanes or reactive esters, for example dimethyl sulphate or diethyl sulphate. The appropriate alkyl iodides have also proved to be useful for this purpose. It depends upon the reaction conditions whether the α- or β-position of the digitoxose residue is preponderantly alkylated. If the methylation is carried out in the presence of aluminum isopropylate in dimethyl formamide with methyl iodide, then the introduction of the methyl radical into the digitoxose residue takes place preponderantly in the α-position; whereas in the case of methylation with dimethyl sulfate in dimethyl formamide and an inert solvent in the presence of strontium hydroxide and aluminum oxide, the β-position is preponderantly methylated. As inert solvents, there can be used all solvents which are miscible with dimethyl formamide and which are not attacked by dimethyl sulfate under the reaction conditions; the amount of solvent to be used must be determined from case to case but an amount equivalent to the amount of dimethyl formamide used has proved to be favorable. Toluene has proved to be especially useful for this purpose. In addition, benzene, dioxan, cyclohexane and chlorinated hydrocarbons, for example, ethylene chloride or chloroform, can also be used.

If one or two of the groups $R_1$, $R_2$ or $R_3$ of the compounds of the general formula (I) are to be acetyl radicals, these can be introduced before or after the hydrogenation or alkylation in known manner. Acetyl radicals can be simply introduced when digoxin derivatives with free hydroxyl groups are reacted with one of the acetylation agents conventional in sugar chemistry, for example, acetic anhydride, acetyl imidazolide, acetyl chloride in pyridine, p-toluene-sulfochloride in pyridine and glacial acetic acid and the like; but care must be taken that not more than one hydroxyl group is esterified in te digitoxose residue. If the acetylation is carried out in the presence of a tertiary amine, for example pyridine, using acetic anhydride, then the reaction takes place at ambient temperature and thus especially gently.

All the derivatives of dihydrodigoxin prepared according to methods (a) to (c) no longer contain non-hydrogenated derivatives of digoxin, as can be ascertained by the negative color reaction of the unsaturated lactone ring with Kedde's reagent and by $R_F$ differences.

The following Examples are given for the purpose of illustrating the preparation of the compounds of the present invention:

EXAMPLE 1 — Preparation of
20,22-Dihydro-4'''-O-methyl-digoxin (process a))

3 g. β-Methyl-digoxin, dissolved in 270 ml. ethanol and 240 ml. dioxan, were, after the addition of 900 mg. platinum oxide, hydrogenated at ambient temperature until the take up of hydrogen ceased (after about 8 hours). Subsequently, the catalyst was filtered off, the filtrate was evaporated in a vacuum and the residue was dissolved in chloroform, decolorized with charcoal, filtered over silica gel, evaporated and the residue was crystallized from acetone-ether-petroleum ether. There were obtained 2.74 g. 20,22-dihydro-4'''-O-methyl-digoxin (dihydro-β-methyl-digoxin); m.p. 151°–155°C.; $R_F$ : 0.27.

The β-methyl-digoxin used as starting material was prepared in the following manner:

10 g. digoxin were dissolved in 77 ml. dimethyl formamide and mixed with 77 ml toluene, 12.3 g. strontium hydroxide and 7.7 g. aluminum oxide (Merck, according to Brockmann). 23.1 ml. dimethyl sulfate in 123 ml. toluene were added at ambient temperature, while stirring. Subsequently, the reaction mixture was further stirred for 4 hours at ambient temperature, diluted with 500 ml. chloroform, filtered with suction over kieselguhr, washed with 300 ml. chloroform, mixed with 120 ml. pyridine and evaporated in a vacuum until a viscous residue remains. This residue was taken up in 300 ml. chloroform and shaken out three times with 50 ml. amounts of water. The collected wash water was again shaken out with chloroform and the combined chloroform phases, after drying over anhydrous sodium sulfate, were evaporated in a vacuum. The dry residue obtained (11.7 g.) was subjected to multiplicative partition with the phase mixture carbon tetrachloride-ethyl acetatemethanol-water (3:1:2:2). The aqueous phase was shaken out with chloroform and evaporated in a vacuum to give 9.4 g. crude product which, for further purification, was dissolved in chloroform containing 2% methanol, and then filtered over 90 g. aluminum oxide (Brockmann). After evaporation of the chloroform/methanol solution, the residue obtained was crystallized from acetone. There were obtained 7.3 g. 4'''-O-methyl-digoxin (β-methyl-digoxin); m.p. 226°–229°C.; $R_F$ : 0.19.

EXAMPLE 2 — Preparation of
20,22-Dihydro-4'''-O-methyl-digoxin (process b))

1 g. 20,22-dihydrodigoxin was dissolved in 10 ml. dimethyl formamide and 10 ml. toluene and mixed with 1.2 g. strontium hydroxide and 0.7 g. aluminum oxide. 2.3 ml. dimethyl sulfate in 12 ml. toluene were added, while stirring, at ambient temperature. Subsequently, the reaction mixture was stirred for 4 hours at ambient temperature and thereafter worked up as described in Example 1. The crude product obtained (0.93 g.) was subjected to multiplicative partition with the phase mixture chloroform-carbon tetrachloride-methanol-water (1:1:1:1). The residue (about 600 mg.) obtained after evaporation of the organic phase was fractionated over silica gel with carbon tetrachloride-ethyl acetate (50–95%). The fractions obtained with 90% ethyl acetate give, after evaporation and crystallization of the residue from acetone-ether-petroleum ether, 450 mg. 20,22-dihydro-4'''-O-methyl-digoxin (dihydro-β-methyl-digoxin); m.p. 149°–153°C.; $R_F$ : 0.27.

EXAMPLE 3 — Preparation of
20,22-Dihydro-3'''-O-methyl-digoxin 1 g. α-methyl-digoxin, dissolved in 45 ml. ethanol and 40 ml. dioxan, was, after the addition of 300 mg. platinum oxide, hydrogenated at ambient temperature until the take up of hydrogen ceases (about 7 hours). Subsequently, the catalyst was filtered off, the filtrate was evaporated in a vacuum and the residue was dissolved in chloroform-methanol (1:1), decolorized with charcoal, filtered over silica gel and the filtrate was evaporated and the residue crystallized from acetone-ether-petroleum ether. There were obtained 850 mg. 20,22-dihydro-3'''-O-methyl-digoxin (dihydro-α-methyl-digoxin); m.p. 129°–132°C.; $R_F$ : 0.27.

The α-methyl-digoxin used as starting material was prepared in the following manner:

4 g. digoxin were dissolved in 40 ml. dimethyl formamide, mixed with 8 g. aluminum isopropylate and 7 ml. methyl iodide and stirred for 65 hours at ambient temperature. Subsequently, 200 ml. methanol and 200 ml. 1N hydrochloric acid were added to the reaction mixture and then immediately shaken out 6 times with 40 ml. amounts of chloroform phases were shaken out twice with 60 ml. amounts of 5% aqueous sodium bicarbonate solution and the chloroform phase was dried over anhydrous sodium sulfate, filtered and evaporated in a vacuum. The residue was subjected to multiplicative partition with the phase mixture chloroform-carbon tetrachloride-methanol-water (1:1:1:1). After evaporation of the organic phase, the residue obtained was crystallized from methanol. There were obtained 2.2 g. 3'''-O-methyl-digoxin (α-methyl-digoxin); m.p. 215°–217°C.; $R_F$ : 0.19.

EXAMPLE 4 — Preparation of 20,22-Dihydro-3''',4'''-dimethyl-digoxin 200 mg. 3''',4'''-dimethyldigoxin were dissolved in 9 ml. ethanol and 8 ml. dioxan and, after the addition of 60 mg. platinum oxide, hydrogenated at ambient temperature until the take up of hydrogen ceases (about 4 hours). Thereafter, the catalyst was filtered off, the filtrate was evaporated in a vacuum and the residue was dissolved in chloroform-methanol (1:1), decolorized with charcoal, filtered over silica gel, evaporated and the residue crystallized from acetone-ether-petroleum ether. There were obtained 170 mg. 20,22-dihydro-3''',4'''-dimethyldigoxin; m.p. 232°–234°C.; $R_F$ : 0.68.

The 3''',4'''-dimethyldigoxin used as starting material was prepared in the following manner:

4 g. digoxin were dissolved in 30 ml. dimethyl formamide and 30 ml. toluene, and mixed with 2 g. zinc hydroxide and 3 g. aluminum oxide. 9.25 ml. dimethyl sulfate in 49 ml. toluene were added thereto, with stirring, at ambient temperature. Subsequently, the reaction mixture was stirred for 18 hours at ambient temperature and, after the addition of chloroform, worked up in the manner described in Example 1. The crude product obtained was subjected to multiplicative partition with the phase mixture carbon tetrachloride-ethyl acetate-methanol-water (3:1:2:2). The organic phase was evaporated and, for further purification, the residue obtained was subjected to a multiplicative partition with the phase mixture carbon tetrachloride-ethyl acetate-methanol-water (9:1:6:4). After shaking out the aqueous phase with chloroform, evaporating in a vacuum and crystallizing from acetone-ether, there were obtained 2.5 g. 3''',4'''-dimethyldigoxin; m.p. 191°–196°C.; $R_F$ : 0.58.

EXAMPLE 5 — Preparation of 20,22-Dihydro-β-ethyl-digoxin.

400 mg. β-ethyl-digoxin were dissolved in 20 ml. ethanol and 16 ml. dioxan and, after the addition of 120 ml. platinum oxide, hydrogenated at ambient temperature until the take up of hydrogen ceases (about 4 hours). Subsequently, the catalyst was filtered off and the filtrate was evaporated. The residue was crystallized from chloroform-ether-petroleum ether. There were obtained 320 mg. 20,22-dihydro-β-ethyl-digoxin; m.p. 132°–135°C.: $R_F$ : 0.52 (β-ethyl-digoxin 0.44).

The preparation of the β-ethyl-digoxin used as starting material was carried out analogously to the method described in Example 1.

EXAMPLE 6 — Preparation of 20,22-Dihydro-12-O-acetyl-β-methyl-digoxin.

100 mg. 12-O-acetyl-β-methyl-digoxin were dissolved in 4.5 ml. ethanol and 4 ml. dioxan and, after the addition of 30 mg. platinum oxide, hydrogenated at ambient temperature until the take up of hydrogen ceases (about 4 hours). Thereafter, the catalyst was filtered off, the filtrate was evaporated in a vacuum and the residue was crystallized from chloroform-ether-petroleum ether. There were obtained 70 mg. 20,22-dihydro-12-O-acetyl-β-methyl-digoxin; m.p. 137°–140°C.; $R_F$ : 0.70.

The 12-O-acetyl-β-methyl-digoxin used as starting material was prepared in the following manner:

1. g. β-methyl-digoxin was dissolved in 5 ml. pyridine, mixed with 130 mg. acetic anhydride and left to stand at ambient temperature for 24 hours. Subsequently, the reaction mixture was diluted with water, shaken out with chloroform, the chloroform phase was washed with 2N sulfuric acid and with water, dried over anhydrous sodium sulfate and evaporated in a vacuum. The crude product thus obtained was subjected to a multiplicative partition with the phase mixture carbon tetrachloride-ethyl acetate-methanol-water (3:1:2:2). After evaporation of the organic phase and crystallization from acetone-ether-petroleum ether, there were obtained 520 mg. 12-O-acetyl-β-methyl-digoxin; m.p. 151°–154°C.; $R_F$ : 0.60.

The $R_F$ values given in the above Examples were all determined on Merck kieselguhr plates. In the case of Examples 1 to 5, the eluent was chloroform-heptane (3:2) and in the case of Example 6, was chloroform-heptane (1:1).

The compounds of this invention are useful in the preparation of medicinal agents because of their cardio-pharmacodynamic actions.

The new compounds of general formula (I) according to the present invention can be administered enterally and parenterally, in admixture with a liquid or solid pharmaceutical diluent or carrier. As injection medium, it is preferred to use water which contains the conventional additives for injection solutions, for example, stabilizing agents, solubilizing agents and buffers. Additives of this kind include, for example, tartrate and citrate buffers, ethanol, complex-forming agents (for example ethylenediamine-tetraacetic acid and the non-toxic salts thereof) and high molecular weight polymers (for example liquid polyethylene oxide) for viscosity regulation. Solid carrier materials include, for example, starch, lactose, mannitol, methyl cellulose, talc, highly-dispersed silicic acids, high molecular weight fatty acids (for example, stearic acid), gelatine, agar-agar, calcium phosphate, magnesium stearate, animal and vegetable fats and solid high molecular weight polymers (for example polyethylene glycols); compositions suitable for oral administration can, if desired, contain flavoring and/or sweetening agents.

The amount of dihydrodigoxin compound present in such preparations may, of course, vary. It is necessary that the active ingredient be contained therein in such an amount that a suitable dosage will be ensured. Ordinarily, the preparations should not contain less than about 0.1 mg of the active dihydro-digoxins. The preferred amount in orally administered preparations such as tablets, pills and the like, is between about 0.2 mg and 1.0 mg per day.

The doses to be administered vary according to the type of action desired, i.e., whether said action is to be digitalization or maintenance. It is, of course, understood that the physician will determine the proper amounts to be given to a patient depending upon the symptoms to be alleviated and the patient's condition and that the doses given above are by no means limiting the new dihydrodigoxin compounds to such dosages.

Digoxin is a well known agent for use in the treatment of cardiac disturbances, i.e., cardiac failure, atrial fibrillation and flutter, paroxysmal tachycardia, cardial insufficiency, etc. It has the advantage as compared to digitoxin that its onset of action is more rapid and is of shorter duration. In this connection it has the further advantage that in the event of an overdose, the symptoms associated therewith are more quickly dissipated. However, it is not as completely absorbed from the G.I. tract as digitoxin. Digoxin is absorbed only to the extent of 60–70%.

In order to establish the effectiveness of the compounds of the invention, i.e., their improved absorption rate, the compounds of the invention and digoxin as comparison compound were administered both intravenously and via the oral route and the absorption determined coincident with the determination of the pharmacological activity.

The criterion which was selected for measuring the effectiveness of the compound was the length of the period of time elapsing following intraduodenal and intravenous injection of the tested compounds in the guinea pig before ventricular extrasystoles and cardiac arrest occurred.

In the guinea pig, a cardiac insufficiency can be produced by application of the known anaesthetic Barbital-Na, which results in a decrease of blood pressure and heart minute volume (SCHAUMANN, W., "Kreislaufwirkungen von g-Strophanthin am normalen und herzinsuffizienten Meerschweinchen"; Naunyn-Schmiedeberg's Arch. exp. Path. u. Pharmak. 247, 229–242 (1964)). The easiest way to determine therapeutic action is by way of the re-increase of the blood pressure.

The first toxic actions of heart glycosides in the guinea pig are in arrhysmia. This corresponds to the toxicity in the human heart. The arrhysmia can be read from the EKG and from the irregularities on the blood pressure curve.

METHOD

Guinea pigs were anaesthetized with 1 g/kg Barbital-Na [5,5-diethyl barbituric acid ("Veronal")] i.p. in 10 ml/kg liquid. Canulas were inserted for intravenous and intraduodenal injection. Under artifical respiration, blood pressure was continuously recorded. After stabilization of the blood pressure, 10 mg/kg of the test compound, dihydro-β-methyl-digoxin, or 2.5 mg/kg of β-methyl-digoxin (for comparison; see U.S. Pat. No. 3,538,078) were intraduodenally injected and the blood pressure was recorded during the next thirty minutes. Systolic and diastolic blood pressure as well as the amplitude of the pulse were measured prior to, as well as 10, 20 and 30 minutes after, the injection. The mean value as well as their mean errors were calculated in accordance with the method of the smallest square deviation.

The results are set forth in Tables 2 and 3 below. The results show that the respective dosages of the two compounds used, viz., 10 mg/kg dihydro-β-methyl-digoxin and 2.5 mg/kg β-methyl-digoxin resulted in the same effect in guinea pigs under Barbital anesthesia.

In the experiments with β-methyl-digoxin, arrhysmia occurred in all animals after 20 ± 3 minutes. However, all animals tolerated 10 mg/kg of dihydro-β-methyl digoxin.

In further experiments, both glycosides were intraduodenally injected in urethane-anesthetized guinea pigs for determining toxicity and the periods until arrhysmia and cardiac arrest occurred were measured. The results are summarized in the following Tables:

TABLE 1

| Glycoside | mg/kg | Arrhysmia | | Cardiac Arrest | |
|---|---|---|---|---|---|
| | | % | min. | % | min |
| β-Methyl-Digoxin | 2,5 | 100 | 11(10–12) | 100 | 24(22–26) |
| | 2,0 | 100 | 18(17–19) | 80 | 30(25–35) |
| | 1,5 | 80 | 20(19–21) | 50 | 67 |
| Dihydro-β-Methyl-Digoxin | 10 | 0 | >120 | 0 | >120 |
| | 20 | 0 | >120 | 0 | >120 |

Urethane has less of a cardiac action than Barbital. Therefore, all animals in urethane-anaesthesia are more sensitive to cardiac glycosides, which is evident from the shorter time of an average of 11 minutes until occurrence of arrhysmia after 2.5 mg/kg β-methyl-digoxin. However, even 20 mg/kg dihydro-β-methyl-digoxin were not toxic.

It is a characteristic of all known cardiac-active glycosides that, in case of intravenous infusion or after intraduodenal injection, they result in arrhysmia and cardiac arrest. Although dihydro-β-methyl-digoxin in a higher dosage has the same therapeutic action as β-methyl-digoxin (see above), it was surprisingly observed that no rhythm disturbances occurred; however, above all, dihydro-β-methyl-digoxin has a centrally stimulating action, which is not characteristic of cardiac glycosides. The animals became restless and threatened to wake up from the anaesthesia. Such an effect has so far only been observed with centrally stimulating compounds.

TABLE 2

Effect of 2.5 mg/kg β-Methyl-Digoxin on the blood pressure of guinea pigs with cardiac insufficiency under "Barbital" anesthesia (each value is the average of values from 5 test animals)

| | Blood Pressure in mm HG | | | |
|---|---|---|---|---|
| | Initial Level | | Increase after | |
| | | 10 | 20 | 30 min. |
| Systolic blood pressure | 35 ± 2 | 13 ± 2 | 23 ± 4 | 17 ± 3 |
| Diastolic blood pressure | 20 ± 2 | 9 ± 2 | 11 ± 3 | 8 ± 3 |
| Pulse amplitude | 15 ± 1 | 4 ± 1 | 12 ± 1 | 8 ± 3 |

TABLE 3

Effect of 10 mg/kg Dihydro-β-Methyl-Digoxin on the blood pressure of guinea pigs with cardiac insufficiency under "Barbital" anesthesia (each value is the average of values from 5 test animals)

| | Blood Pressure in mm HG | | | |
|---|---|---|---|---|
| | Initial Level | | Increase after | |
| | | 10 | 20 | 30 min. |
| Systolic blood pressure | 37 ± 1 | 14 ± 2 | 19 ± 2 | 12 ± 2 |
| Diastolic blood pressure | 21 ± 1 | 7 ± 1 | 10 ± 1 | 7 ± 1 |
| Pulse amplitude | 16 ± 1 | 7 ± 1 | 9 ± 2 | 5 ± 2 |

It will be understood that the specification and examples are illustrative but not limitative of the present invention and that other embodiments within the spirit and scope of the invention will suggest themselves to those skilled in the art.

What is claimed is:

1. Dihydrodigoxin compound of the formula

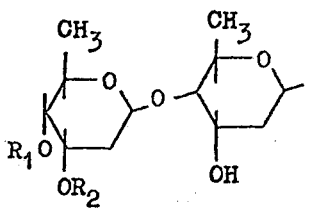

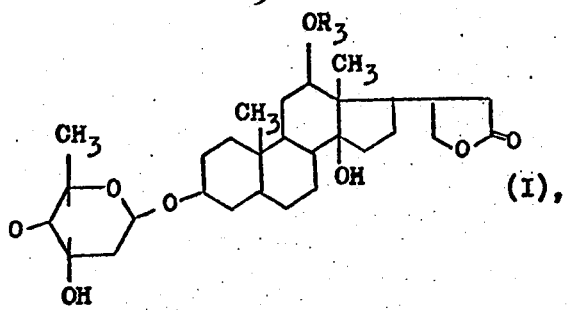

wherein one of $R_1$ and $R_2$ represents a methyl or ethyl radical and the other represents hydrogen, methyl, ethyl or acetyl; and $R_3$ is hydrogen or an acetyl group.

2. Dihydrodigoxin compound as claimed in claim 1 wherein $R_1$ is methyl or ethyl.
3. Dihydrodigoxin compound as claimed in claim 1 wherein $R_2$ is methyl or ethyl.
4. Dihydrodigoxin compound as claimed in claim 2 wherein $R_2$ is hydrogen.
5. Dihydrodigoxin compound as claimed in claim 3 wherein $R_1$ is hydrogen.
6. Dihydrodigoxin compound as claimed in claim 2 wherein $R_2$ is methyl or ethyl.
7. Dihydrodigoxin compound as claimed in claim 3 wherein $R_1$ is methyl or ethyl.
8. Dihydrodigoxin compound as claimed in claim 2 wherein $R_2$ is acetyl.
9. Dihydrodigoxin compound as claimed in claim 3 wherein $R_1$ is acetyl.
10. Dihydrodigoxin compound as claimed in claim 1 designated 20,22-Dihydro-4'''-O-methyl-digoxin.

* * * * *